United States Patent [19]

Kahan et al.

[11] Patent Number: 5,179,008
[45] Date of Patent: Jan. 12, 1993

[54] HYBRIDOMA AND MONOCLONAL ANTIBODY TO FHAP

[75] Inventors: Lawrence Kahan; Frank C. Larson, both of Madison, Wis.

[73] Assignee: Wisconsin Alumni Research Foundation, Madison, Wis.

[21] Appl. No.: 604,715

[22] Filed: Oct. 26, 1990

Related U.S. Application Data

[62] Division of Ser. No. 308,238, Feb. 9, 1989, Pat. No. 5,001,052.

[51] Int. Cl.$^5$ .............. C07K 3/00; C07K 15/00; C12N 5/16
[52] U.S. Cl. .............. 435/70.21; 435/240.27; 530/388.26
[58] Field of Search .............. 435/172.1, 172.2, 70.21, 435/240.27; 530/387, 388.26

[56] References Cited

U.S. PATENT DOCUMENTS

| | | |
|---|---|---|
| 4,132,769 | 1/1979 | Osther . |
| 4,150,149 | 4/1979 | Wolfsen et al. . |
| 4,166,766 | 9/1979 | Metzenberg et al. .............. 435/21 |
| 4,379,839 | 4/1983 | Spiegelman et al. . |
| 4,444,890 | 4/1984 | Burzynski . |
| 4,469,787 | 9/1984 | Woods et al. . |
| 4,478,815 | 10/1984 | Burchiel et al. . |
| 4,489,167 | 12/1984 | Ochi et al. . |
| 4,782,015 | 11/1988 | Allison et al. .............. 435/172.2 |
| 4,828,986 | 5/1989 | Smith et al. .............. 435/172.2 |

OTHER PUBLICATIONS

Lattime—Chem. Abst. vol. 104 (1986) p. 84394h.
Ehrmeyer et al—Cancer Research vol. 39 (Mar. 1978) pp. 599–601.
Davis et al—Cancer Research vol. 41 (Mar. 1981) pp. 1110 and 1113.
Mulivor et al—Chem. Abst. vol. 102 (1985) p. 162,655u.
Lawson et al—Chem. Abst. vol. 102 (1985) p. 162,646s.
Bailyes et al—Chem. Abst. vol. 102 (1985) p. 108,548y.
Katzmann et al—Chem. Abst. vol. 105 (1986) p. 129,966k.
PCT Search Report dated Jun. 18, 1990 in connection with PCT Application U.S. 90/00732.
T. Hada et al., 67 Biol. Abstr. (6):36147 (1978).
G. Leyhausen et al., 99 Chem. Abstr. 65000b (1983).
T. Davis et al., 72 Biol. Abstr. (2):10748 (1981).
K. Shinkai et al., 32 Can. Res. 2307–2313 (1972).
R. Bowser-Finn et al., 7 Tumour Biology 343–352 (1986).
F. Larson et al., 2 J. Clin. Oncol. 457–461 (1984).
L. Kahan et al., 27 Clin. Chem. 104–107 (1981).
M. Viot et al., 52 Cancer 140–145 (1983).
C. Karmen et al., 37 J. Clin. Pathol. 212–217 (1984).
H. Nishio et al., 57 Cancer 1815–1819 (1986).
M. De Broe et al., 5 Hepatology 118–128 (1985).
E. Schonau et al., 24 J. Clin. Chem. Clin. Biochem. 641–646 (1986).
V. Van Hoof et al., 34 Clin. Chem. 1857–1862 (1988).
P. Emmelot et al., 150 Biochim. Biophys. Acta. 364–375 (1968).
R. Singer et al., 35 Can. Res. 3048–3050 (1975).
M. De Broe et al., 59 Clin. Chim. Acta. 369–372 (1975).
M. De Broe et al., 81 Clin. Chim. Acta. 237–245 (1977).
P. Ey et al., 15 Immunochemistry 429–436 (1978).
J. Deng et al., 176 Clin. Chim. Acta 291–302 (1988).

*Primary Examiner*—Sam Rosen
*Attorney, Agent, or Firm*—Quarles & Brady

[57] ABSTRACT

Antibodies, hybridomas, and immunoassays relating to a fast homoargenine-sensitive alkaline phosphatase cancer complex in serum ("FHAP") are disclosed. FHAP is a disease (e.g. cancer) marker. One aspect of the disclosure is the measuring of the physical association of two different components of FHAP as part of the assay.

6 Claims, No Drawings

HYBRIDOMA AND MONOCLONAL ANTIBODY TO FHAP

This is a division of application Ser. No. 07/308,238, filed Feb. 9, 1989 now U.S. Pat. No. 5,001,052.

This invention relates generally to an immunoassay for FHAP (a cancer marker) in serum. More particularly it relates to measuring the physical association of two FHAP constituents as an indicator of disease.

BACKGROUND OF THE INVENTION

The blood of persons having diseases involving tissue degeneration often contains elevated levels of membrane fragments. See generally K. Shinkai et al., 32 Can. Res. 2307–2313 (1972). The disclosure of this article and of all other articles and patents referred to herein are incorporated by reference as if fully set forth herein. One such fragment, "FHAP", has been separated by electrophoresis (see e.g. U.S. Pat. No. 4,166,766) and was first detected by its alkaline phosphatase activity. Its unique (fast) electrophoretic mobility and its sensitivity to inhibition by homoarginine are the basis of its acronym. In this regard, FHAP is faster than liver alkaline phosphatase in certain types of cellulose acetate electrophoresis.

The acronym "FHAP" was originally developed to name a complex that is the fast homarginine-sensitive alkaline phosphatase cancer marker described in U.S. Pat. No. 4,166,766. The complex was originally thought to be an isoenzyme. It has now been learned by the applicants that while the FHAP complex does contain the alkaline phosphatase enzyme, it also contains other enzymes. Nevertheless, the acronym has continued to be used to refer to the complex and is used in that manner herein.

Research has shown that FHAP is a marker for a wide variety of cancers. See e.g. R. Bowser-Finn et al., 7 Tumour Biology 343–352 (1986). While FHAP was initially assumed to be an isoenzyme, the substance is in fact a large complex containing, inter alia, alkaline phosphatase, leucine aminopeptidase, gamma-glutamyl transferase and 5' nucleotidase. Since these enzymes are enzymes present in membranes, it is now believed that FHAP is comprised of fragments of cell membranes that are generated during various stages of certain diseases.

While FHAP levels in serum may be measured by cellulose polyacetate electrophoresis, the relatively poor sensitivity of this method limits it usefulness to a small number of cases in which the FHAP concentration approaches the free liver/bone/kidney alkaline phosphatase concentration. FHAP levels in serum may also be measured by an ion-exchange separation and the enzyme assay detailed in U.S. Pat. No. 4,166,766. However, this requires a substantial amount of serum per determination and undue cost and time. Also, the sensitivity of the assay may in some cases permit detection of FHAP-like material which is present in the serum of healthy controls.

Attempts have been made to develop antibodies to FHAP as a first step towards developing immunoassays. However, prior to the present invention these efforts have proved unsuccessful. A further problem is that while prior art assays gave information as to quantitative levels, they told little about the type of cancer or the stage of cancer. Thus, a need exists for a FHAP test which provides a greater amount of information about the disease and which is easier to use.

SUMMARY OF THE INVENTION

The invention provides an antibody to FHAP. The invention also provides a hybridoma capable of producing antibodies to FHAP, preferably monoclonal antibodies.

Another aspect of the invention provides an assay. In a preferred form, one exposes a specimen (e.g. human blood serum) to a compound (e.g. an antibody) which recognizes a first part of FHAP. One then determines the presence in the specimen of a second, different part of FHAP and the degree to which it is physically associated with the first portion. One then compares the assay results against control levels to provide an indication of the likelihood disease.

In an especially preferred form, prior to the exposing step mouse antibody to FHAP has been provided and it has been anchored to a solid surface (e.g. a well). One can do this by directly absorbing the antibody to the well or by using sheep anti-mouse IgG to like the mouse antibody to the well, with the anti-mouse IgG being pre-attached to the well. During the exposing step the FHAP first portion becomes bound to the mouse antibody (and thus is attached to the well). Since the first FHAP portion remains bound to the FHAP second portion, the second FHAP portion is then also "dragged" out of solution. As an alternative to coated wells, a precipitating compound can be linked to the antibody before or after the antibody is exposed to the FHAP.

The determining step preferably involved measuring alkaline phosphatase enzyme activity of material bound to the well. Since one antibody which was found was not directed tot he alkaline phosphatase, this determining step resulted in the measurement of the association of two different FHAP parameters. This may give greater insight into the origin and stage of the cancer, and significantly reduces false positives because it minimizes interference from free alkaline phosphatase.

It should be appreciated that prior attempts to screen for antibodies to FHAP were unsuccessful. One aspect of the invention was therefore to design a means for detecting hybridomas that produce the antibodies. It was discovered that using a detergent as a screening aid was required. The objects of the invention therefore include: (a) providing antibodies and hybridomas of the above kind; (b) providing an immunoassay of the above kind; and (c) providing assays of the above kind which are inexpensive to use, reliable, and informative. These and still other objects and advantages of the invention will be apparent from the description below.

PREFERRED EMBODIMENTS

A. Obtaining A Sample Of FHAP

One method of isolating FHAP is described in U.S. Pat. No. 4,166,766. Another preferred technique is: 1. Dialysis of human blood serum v. 100 mM NaCl, 20 mM Tris (pH 8 at 4°), 1 mM $MgCl_2$, 20 $\mu$M ZnCl; 18 h, 4° C., 600 volumes dialysis buffer. 2. Centrifuge $7000 \times g$ (15 min). 3. Gel filtration on Sephacryl S-400 column ($74 \times 10$ cm) at 600 ml/hr. 4. Pooled void volume fractions applied to $30 \times 1.6$ cm DEAE-Sephacel column. Wash with 200 ml of sample buffer. Elute with 0.1–0.6M NaCl linear gradient. 5. Pool highest specific activity material.

B. Obtaining An Antibody To FHAP

While several techniques of hybridoma and antibody creation are now well know (see generally P. Ey et al., 15 Immunochemistry 429–436 (1978)), attempts to screen for antibodies to FHAP had previously proved unsuccessful. To overcome these problems, the following procedure was used:

1. Immunize a BALB/c mouse with partially purified FHAP.
2. Remove mouse spleen and fuse spleen cells with $NS^{-1}$ myeloma cells using standard techniques.
3. Detect hybridoma cells which produce antibodies to FHAP by screening candidate antibodies as follows:
   (a) Coat polystrene microtiter plates with sheep anti-mouse IgG(SAMIgG).
   (b) Add 10% by volume of 10% Triton X-100 (a detergent) to tissue culture supernatants (new step).
   (c) Incubate tissue culture supernatant (0.1 ml) in the wells of the SAMIgG coated plates.
   (d) Wash the plate.
   (e) Add pooled human serum known to contain high levels of FHAP.
   (f) Wash the plate.
   (g) Add 0.2 mg/ml 4-methyl-umbelliferyl phosphate in 1.0M 2-amino-2-methyl-1-propanol, pH 9.9 containing 20 $\mu M$ $ZnCl_2$ and 1.0 mM $MgCl_2$ (this causes increasing fluorescence as a function of time in the presence of alkaline phosphatase, which FHAP has).
   (h) Measurement fluorescence levels at 0 minutes and 90 minutes. Compute the difference in fluorescence.
   (i) The test is positive if the computed difference is significantly elevated above the difference observed with negative control media (tissue culture supernatant from NS-1 cells).

Note the use of the unique screening agent, Triton X-100, a detergent. It was discovered that detergent must be used because mouse hybridomas naturally release membrane fragments when growing in culture. Fragments from the hybridomas will therefore have immunoglobulins and alkaline phosphatase and thus will give false positive results, regardless of the specifically of the antibody, using screening tests based on alkaline phosphatase. The triton X-100 disrupts the mouse membrane fragments — separating the immunoglobulin and the alkaline phosphatase (and then the detergent and the alkaline phosphatase are washed away at step e). In this way, only antibodies which bind fragments with alkaline phosphatase from the human serum added in step (e) are detected.

A preferred hybridoma was deposited as ATCC HB9643 on Feb. 8, 1988 at the American Type Culture Collection, Rockville, Md., U.S.A., with viability confirmed Feb. 10, 1988. The culture will be made available as required by applicable patent law. Such availability is not intended as a license. The strain is designated as Anti-FHAP Murine hybridoma K 160C2-D2.1G. The antibody it produces recognizes the leucine aminopeptidase portion of FHAP.

C. Immunoassay

We coated 96 Well Flow Laboratories Titertek polystyrene EIA plates with the purified K160C2-D2 antibody. The antibody was dissolved at 10 micrograms per ml in 0.15M NaCl, 0.10M tris(hydroxymethyl)aminomethane buffer, pH 9.0 at 25° C. We then added 0.1 ml antibody solution to each well in columns 3, 4, 7, 8, 11 and 12, and then vortex mixed the plate on a Bellco Miniorbital Shake for 5 seconds at speed 7. After this, we covered the plates and placed them in a sealed plastic bag and incubated the plates 15-18 hours at 25° C. Thereafter, we washed the plates five times with 0.15M NaCl, 0.10M tris(hydroxymethyl)aminomethane buffer, ph 9.0. We then inverted the plates and pounded them on paper towel to remove residual buffer and then air dried plates and stored them covered at 4° C. The wells are of a type where the antibody absorbs directly to the plastic wells.

To run the assay, one dilutes blood serum 20-fold with solution A (0.15M NaCl, 0.05M tris(hydroxymethyl)aminomethane buffer, pH 7.4 at 25° C., 0.001M $MgCl_2$, 0.02 mM $ZnCl_2$, 0.0046M $NaN_3$, 2.5 g/L gelatin). A positive control serum should be appropriately diluted with the same buffer (e.g. 120-fold). One then dispenses 0.2 ml samples into each of four adjacent wells in the same row (e.g. B1, B2, B3, and B4), dispenses 0.2 ml solution A in wells A1, A2, A3, and A4, and dispenses 0.2 ml diluted positive control in wells H9, H10, H11, and H12. Thereafter, one covers and vortex mixes at speed 7 for 5 seconds, and incubates in a water saturated atmosphere at 25° C. for 40-42 hours. Note that the dilution of the sample is required to minimize interference from free FHAP antigen in serum samples (in this case non-FHAP bound leucine aminopeptidase).

The next step is to wash away any unbound materials. To do this, one inverts the plate and shakes out the sample solutions. One then pounds the plate once on a paper towel and washes the plate five time with solution B (0.15M NaCl, 0.05M tris(hydroxymethyl)aminomethane buffer, pH 7.4 at 25° C., 0.001M $MgCl_2$, 0.02 mM $ZnCl_2$, 0.0046M $NaN_3$) using an automatic plate washer. Thereafter, one pounds the plate once on a paper towel.

Next, one measures the presence of a different protein (or non-protein antigen) which is physically associated with the antigen recognized by the antibody that is bound to the solid surface. This substance may be an enzyme, a protein antigen, or a non-protein antigen which is noncovalently associated with the protein antigen recognized by the antibody. The preferred system is to measure alkaline phosphatase enzyme activity of the compounds bound to the well by dispensing 0.2 ml of solution C (0.2 mg/ml sodium 4-methylumbelliferyl phosphate, 1M 2-amino 2-methyl 1-propanol, pH 10.3 at 25° C., 0.001M $MgCl_2$, 0.020 mM $ZnCl_2$) into each well. One then dispenses 0.2 ml solution C into several wells of another plate and adds 0.01 ml diluted control serum to each well (e.g. Sigma Chemical Company 2N Enzyme Control diluted 64-fold or 128-fold with solution A).

After incubating 240 minutes in the dark at 25° C. one measures the fluorescence in each well, exciting with light at 340 to 400 nm and measuring emission at 450 nm. Both the Dynatech Laboratories, Inc. Microfluor Reader and the Flow Laboratories Titertek Fluoroskan are suitable instruments. For each sample, one calculates the differences between the average of the two values for the wells which were coated with antibody and the average of the two values for the wells which were not coated (e.g. [B3+B4−B1−B2]/2). Note that the second compound could also be measured by immunological techniques (such as by the binding of a radioactive or enzyme conjugated antibody specific for the second protein) or by other means.

Finally, one compares the amount of physically associated second compound with the upper limit of normal. In the above example, the upper limit of normal controls was 0.2 IU/L alkaline phosphatase associated with the antigen recognized by antibody K160C2D-2. Higher concentrations of alkaline phosphatase associated with this antigen are frequently observed in individuals with cancer, hepatitis, and diabetes.

Improvements achieved in the above example over previous methods include a reduction in sample required, elimination of an ion exchange, electrophoretic or gel filtration separation step, and improved specificity. Moreover, it is hoped that use of this assay in combination further analysis of the composition of the membrane fragments in individual patient serum samples will lead to information relating to the origin or state of the disease.

The invention is not limited to use of any single antibody or hybridoma, or even just to those derived (e.g. directly or indirectly derived) therefrom. Thus, the invention is not to be limited to just the preferred embodiments. Rather, the claims should be referred to in assessing the full breadth of the invention.

We claim:

1. A monoclonal antibody to FHAP.
2. The antibody of claim 1 wherein the antibody is also an antibody to leucine aminopeptidase.
3. The antibody of claim 1, wherein the antibody was derived from the hybridoma of ATCC HB9643 or the progeny of ATCC HB9643.
4. A hybridoma capable of producing a monoclonal antibody to FHAP.
5. The hybridoma of claim 4, wherein the antibody it is capable of producing also is an antibody to leucine aminopeptidase.
6. The hybridoma of claim 4, wherein the hybridoma was derived from ATCC HB9643 or the progeny of HB9643.

* * * * *